(12) United States Patent
Lee et al.

(10) Patent No.: US 7,807,197 B2
(45) Date of Patent: Oct. 5, 2010

(54) COMPOSITE DOSAGE FORMS HAVING AN INLAID PORTION

(75) Inventors: Der-Yang Lee, Flemington, NJ (US); Harry S. Sowden, Glenside, PA (US); Martin Thomas, Lake Worth, FL (US)

(73) Assignee: McNeil-PPC, Inc., Skillman, NJ (US)

( * ) Notice: Subject to any disclaimer, the term of this patent is extended or adjusted under 35 U.S.C. 154(b) by 1393 days.

(21) Appl. No.: 10/476,388

(22) PCT Filed: Sep. 28, 2002

(86) PCT No.: PCT/US02/31063

§ 371 (c)(1), (2), (4) Date: Apr. 1, 2004

(87) PCT Pub. No.: WO03/026628

PCT Pub. Date: Apr. 3, 2003

(65) Prior Publication Data

US 2004/0156902 A1    Aug. 12, 2004

(51) Int. Cl.
A61K 9/20 (2006.01)
A61K 9/28 (2006.01)
A61K 9/24 (2006.01)

(52) U.S. Cl. ...................... 424/473; 424/467

(58) Field of Classification Search ................ 424/467
See application file for complete search history.

(56) References Cited

U.S. PATENT DOCUMENTS

| | | |
|---|---|---|
| 599,865 A | 3/1898 | Richards |
| 2,307,371 A | 1/1943 | Hileman |
| 2,996,431 A | 8/1961 | Barry |
| 3,085,942 A | 4/1963 | Magid et al. |
| 3,146,169 A | 8/1964 | Stephenson et al. |
| 3,627,583 A | 12/1971 | Troy et al. |
| 3,760,804 A | 9/1973 | Higuchi et al. |
| 3,832,252 A | 8/1974 | Higuchi et al. |
| 4,097,606 A | 6/1978 | Chavkin et al. |
| 4,139,589 A | 2/1979 | Beringer et al. |
| 4,173,626 A | 11/1979 | Dempski et al. |
| 4,198,390 A | 4/1980 | Rider |
| 4,230,693 A | 10/1980 | Izzo et al. |
| 4,271,206 A | 6/1981 | Fariel et al. |
| 4,322,449 A | 3/1982 | Voss et al. |
| 4,362,757 A | 12/1982 | Chen et al. |
| 4,371,516 A | 2/1983 | Gregory et al. |
| 4,372,942 A | 2/1983 | Cimiluca |
| 4,425,332 A | 1/1984 | James |
| 4,473,526 A | 9/1984 | Buhler et al. |
| RE31,764 E | 12/1984 | Voss et al. |
| 4,518,335 A | 5/1985 | Pujari |
| 4,661,521 A | 4/1987 | Salpekar et al. |
| 4,686,212 A | 8/1987 | Ducatman et al. |
| 4,749,575 A | 6/1988 | Rotman |
| 4,757,090 A | 7/1988 | Salpekar et al. |
| 4,762,719 A | 8/1988 | Forester |
| 4,781,714 A | 11/1988 | Eckenhoff et al. |
| 4,816,262 A | 3/1989 | McMullen |
| 4,820,524 A | 4/1989 | Berta |
| 4,851,226 A | 7/1989 | Julian et al. |
| 4,863,742 A | 9/1989 | Panoz et al. |
| 4,882,167 A | 11/1989 | Jang |
| 4,894,236 A | 1/1990 | Jang |
| 4,906,478 A | 3/1990 | Valentine et al. |
| 4,929,446 A | 5/1990 | Bartolucci |
| 4,980,169 A | 12/1990 | Oppenheimer et al. |

(Continued)

FOREIGN PATENT DOCUMENTS

DE        27 10 307        9/1977

(Continued)

OTHER PUBLICATIONS

International Search Report dated Jan. 8, 2004 for corresponding PCT/US03/08891.
Catellani, P.L. et al., "Centrifugal die fillign system in a new rotary tablet machine", International Journal of Pharmeutics, 88 (1992), pp. 285-291.
Cuff, George et al., "A Preliminary Evaluation of Injection Moldign as a Technology to Produce Tablets", Pharmaceutical Technology, Jun. 1998, pp. 96-106.
Lachman, Leon et al., "Chapter II—Tablets", The Theory and Practice of Industrial Pharmacy, (1986), pp. 293-345.
Eith, L., et al., "Injection-Moulded Drug-Delivery Systems", Manufacturing Chemist (Jan. 1987), pp. 21-25.

(Continued)

*Primary Examiner*—Michael G Hartley
*Assistant Examiner*—Nabila G Ebrahim
(74) *Attorney, Agent, or Firm*—David Crichton

(57) ABSTRACT

A dosage form comprises at least one active ingredient, a first portion which comprises an exterior surface and one or more cavities defining at least one interior surface having indentations and an exterior surface, and a second molded portion which is inlaid into the cavities of the first portion and has an exterior surface. The first and second portions are in contact at an interface, the second portion comprises a solidified thermoplastic material, and the second portion resides substantially conformally upon the indentations of the first portion. In another embodiment, a dosage form comprises at least one active ingredient, a core having an outer surface and a shell residing on at least a portion of the core outer surface, wherein the shell comprises a first shell portion and a second molded shell portion which is inlaid into the first shell portion. In another embodiment, a dosage form comprises at least one active ingredient, a core, and a shell having a first molded shell portion which is discontinuous, and a second molded shell portion which is continuous, such that the discontinuities of the first shell portion are due to the presence of the second molded shell portion, and the first and second shell portions are compositionally different.

41 Claims, 5 Drawing Sheets

U.S. PATENT DOCUMENTS

| | | | |
|---|---|---|---|
| 4,980,170 A | 12/1990 | Schneider et al. | |
| 4,984,240 A | 1/1991 | Keren-Zvi et al. | |
| 4,999,226 A | 3/1991 | Schock et al. | |
| 5,002,970 A | 3/1991 | Eby, III | |
| 5,075,114 A | 12/1991 | Roche | |
| 5,089,270 A | 2/1992 | Hampton et al. | |
| 5,133,892 A | 7/1992 | Chun et al. | |
| 5,146,730 A | 9/1992 | Sadek et al. | |
| 5,169,645 A | 12/1992 | Shukla et al. | |
| 5,188,840 A | 2/1993 | Iida et al. | |
| 5,200,191 A | 4/1993 | Steele et al. | |
| 5,200,193 A | 4/1993 | Radebaugh et al. | |
| 5,213,738 A | 5/1993 | Hampton et al. | |
| 5,213,808 A | 5/1993 | Ba-Shalom et al. | |
| 5,228,916 A | 7/1993 | Berta | |
| 5,229,164 A | 7/1993 | Pins et al. | |
| 5,275,822 A | 1/1994 | Valentine et al. | |
| 5,286,497 A | 2/1994 | Hendrickson et al. | |
| 5,368,863 A | 11/1994 | Eckenhoff et al. | |
| 5,391,378 A | 2/1995 | Sanderson | |
| 5,405,642 A | 4/1995 | Gilis et al. | |
| 5,415,868 A | 5/1995 | Smith et al. | |
| 5,436,026 A | 7/1995 | Berta | |
| 5,456,920 A | 10/1995 | Matoba et al. | |
| 5,459,983 A | 10/1995 | Sadek et al. | |
| 5,464,631 A | 11/1995 | Hoover et al. | |
| 5,489,436 A | 2/1996 | Hoy et al. | |
| 5,511,361 A | 4/1996 | Sauter | |
| 5,538,125 A | 7/1996 | Berta | |
| 5,558,879 A | 9/1996 | Chen | |
| 5,578,336 A | 11/1996 | Monte | |
| 5,593,696 A | 1/1997 | McNally et al. | |
| 5,609,010 A | 3/1997 | Sauter | |
| 5,614,207 A | 3/1997 | Shah et al. | |
| 5,679,406 A | 10/1997 | Berta | |
| 5,681,584 A | 10/1997 | Savastano et al. | |
| 5,711,961 A | 1/1998 | Reiner et al. | |
| 5,738,874 A | 4/1998 | Conte et al. | |
| 5,795,588 A | 8/1998 | Sauter | |
| 5,807,579 A | 9/1998 | Vilkov et al. | |
| 5,824,338 A | 10/1998 | Jacobs et al. | |
| 5,827,535 A | 10/1998 | Stone | |
| 5,830,501 A | 11/1998 | Dong et al. | |
| 5,830,502 A | 11/1998 | Dong et al. | |
| 5,853,760 A | 12/1998 | Cremer | |
| 5,871,781 A | 2/1999 | Myers et al. | |
| 5,912,013 A | 6/1999 | Rudnic et al. | |
| 5,942,034 A | 8/1999 | Brehant et al. | |
| 5,980,944 A | 11/1999 | Stevens et al. | |
| 5,997,905 A | 12/1999 | McTeigue et al. | |
| 6,001,391 A | 12/1999 | Zeidler et al. | |
| 6,103,257 A | 8/2000 | Nisonoff | |
| 6,103,260 A | 8/2000 | Luber et al. | |
| 6,110,499 A | 8/2000 | Shivanand et al. | |
| 6,117,479 A | 9/2000 | Hogan et al. | |
| 6,123,861 A * | 9/2000 | Santini et al. | 216/2 |
| 6,149,939 A * | 11/2000 | Strumor et al. | 424/464 |
| 6,149,943 A | 11/2000 | McTeigue et al. | |
| 6,200,590 B1 | 3/2001 | Eley | |
| 6,248,760 B1 | 6/2001 | Wilhelmsen | |
| 6,270,805 B1 | 8/2001 | Chen et al. | |
| 6,294,200 B1 | 9/2001 | Conte et al. | |
| 6,322,819 B1 | 11/2001 | Burnside et al. | |
| 6,350,398 B1 | 2/2002 | Breitenbach et al. | |
| 6,365,185 B1 | 4/2002 | Ritschel | |
| 6,372,252 B1 | 4/2002 | Blume et al. | |
| 6,394,094 B1 | 5/2002 | McKenna et al. | |
| 2001/0001280 A1 | 5/2001 | Dong et al. | |
| 2002/0028240 A1 | 3/2002 | Sawada et al. | |
| 2002/0051807 A1 | 5/2002 | Faour et al. | |
| 2003/0068367 A1 | 4/2003 | Sowden | |
| 2003/0068373 A1 | 4/2003 | Sowden | |
| 2003/0070903 A1 | 4/2003 | Sowden | |
| 2003/0072799 A1 | 4/2003 | Sowden | |
| 2003/0086973 A1 | 5/2003 | Sowden | |
| 2003/0124183 A1 | 7/2003 | Sowden | |

FOREIGN PATENT DOCUMENTS

| | | |
|---|---|---|
| DE | 198 34 180 A1 | 2/2000 |
| DE | 199 54 420 A1 | 5/2001 |
| DE | 199 63 569 A1 | 7/2001 |
| EP | 0 088 556 B1 | 9/1983 |
| EP | 0 060 023 B1 | 8/1984 |
| EP | 0 239 983 B1 | 10/1987 |
| EP | 0 325 492 A1 | 7/1989 |
| EP | 0 088 556 B1 | 9/1989 |
| EP | 0 387 885 B1 | 9/1990 |
| EP | 0 455 599 A1 | 11/1991 |
| EP | 0 294 993 B1 | 12/1991 |
| EP | 0 861 659 A1 | 2/1992 |
| EP | 0 481 547 A1 | 4/1992 |
| EP | 0 531 524 B1 | 3/1993 |
| EP | 0 572 731 A1 | 12/1993 |
| EP | 0 788 790 A2 | 2/1996 |
| EP | 0 740 938 B1 | 11/1996 |
| EP | 0 864 324 B1 | 3/1997 |
| EP | 0 950 402 B1 | 2/1999 |
| EP | 1 029 892 B1 | 8/2000 |
| EP | 1 077 065 A1 | 2/2001 |
| FR | 2 604 904 A1 | 4/1988 |
| GB | 759081 | 10/1956 |
| GB | 994 742 | 5/1961 |
| GB | 888 038 | 1/1962 |
| GB | 936 386 | 9/1963 |
| GB | 1 144 915 | 3/1969 |
| GB | 1 372 040 | 10/1974 |
| GB | 1 464 388 | 2/1977 |
| GB | 2 197 778 A | 6/1988 |
| GB | 2 284 760 A | 6/1995 |
| NL | 86 602 556 | 5/1988 |
| WO | WO 89/11968 | 12/1989 |
| WO | WO 94/06416 A1 | 3/1994 |
| WO | WO 94/07470 A1 | 4/1994 |
| WO | WO 95/02396 A1 | 1/1995 |
| WO | WO 95/15156 A1 | 6/1995 |
| WO | WO 97/06695 A1 | 2/1997 |
| WO | WO 97/15293 A2 | 5/1997 |
| WO | WO 98/20870 A1 | 5/1998 |
| WO | WO 99/02136 A1 | 1/1999 |
| WO | WO 99/32092 A1 | 7/1999 |
| WO | WO 99/51209 A1 | 10/1999 |
| WO | WO 99/56730 A1 | 11/1999 |
| WO | WO 00/18447 A2 | 4/2000 |
| WO | WO 00/25755 A1 | 5/2000 |
| WO | WO 01/49815 A2 | 7/2001 |
| WO | WO 01/57144 A1 | 8/2001 |
| WO | WO 02/11702 A2 | 2/2002 |
| WO | WO 02/19833 A2 | 3/2002 |

OTHER PUBLICATIONS

Elizabeth Carbide Die Co. Inc., The Elizabeth Companies Tablet Design Training Manual, McKeesport, PA Gunsel, William C., et al., "Compression-Coated and Layer Tablets", Pharmaceutical Dosage Forms, Tablets, $2^{nd}$ ed., 1989, pp. 247-284, vol. 1, Marcel Dekker, Inc., New York.

Rosato, Dominick V., et al., Injection Molding Handbook, 1986, Van Nostrand Reinhold Company, Date: 1986.

* cited by examiner

COMPOSITE DOSAGE FORMS HAVING AN INLAID PORTION

This application claims the benefit of U.S. Ser. Nos. 09/966,939, 09/966,509, 09/966,497, 09/967,414, and 09/966,450, all filed on Sep. 28, 2001.

BACKGROUND OF THE INVENTION

1. Field of the Invention

This invention relates to composite dosage forms such as pharmaceutical compositions. More particularly, this invention relates to composite dosage forms comprising at least one active ingredient and having a first portion and a molded second portion which is inlaid.

2. Background Information

Coated tablets, such as film coated tablets, sugar coated tablets, gelcaps, and geltabs are used as solid oral dosage forms, having improved aesthetics, stability and swallowability compared to uncoated tablets. It is particularly useful to provide unique aesthetic features to solid dosage forms to aid with their identification and differentiation in the marketplace. Film coatings and sugar coatings are typically applied by spraying in a rotating pan, and while they may be formulated in a variety of colors, generally only one color can be applied around the entirety of a tablet core. Gelcaps and geltabs have been prepared by dip-coating, enrobing, and shrink-fitting of capsule shells onto the surface of a tablet core. These methods enable the use of multiple colors, however suffer from other limitations.

Film formulations for producing gelcaps and geltabs prepared via enrobing methods such as those disclosed in U.S. Pat. Nos. 5,146,730 and 5,459,983 typically comprises a water-based gelatin preparation having about 45% gelatin and about 9% plasticizer (glycerin and/or sorbitol) by weight. The plasticizer has been reported to play a critical role in such formulations. Low ratios of plasticizer to gelatin result in a brittle coating around the tablet core, while high ratios result in a gelatin coating around the tablet which is flexible and can be peeled from the tablet. If a gelatin coating that adheres to the product core is desired, then gelatin formulations having by-weight compositions of 40 percent to 60 percent gelatin, 5 percent to 12 percent plasticizer, 35 percent to 50 percent water, and colorants and pigments in the range of 0.1 percent to 3 percent should be considered. Glycerin and sorbitol can be used as single plasticizers or in combination with each other. In addition, other sugars and poly-hydroxy compounds can be used as additives and plasticizers. If a tamper-evident gelatin-coated medicine tablet is the desired end product, then the ratio of plasticizer to gelatin in the gelatin formulation should be in the range of about 1:5. The need for such plasticizers at such levels imparts limitations to enrobed dosage forms, including a propensity to absorb moisture, which may compromise the physical and chemical stability of the product, as well adding cost to the formulation.

Another current method for forming a shell (or coating) on a core (or substrate) is that disclosed in WO 01/57144 which utilizes the principles of electrostatic deposition to form the coating. This method suffers from the limitation that at least one of the core or the shell must incorporate one or more "charge control agents", such as metal salicylates, for example zinc salicylate, magnesium salicylate and calcium salicylate; quaternary ammonium salts; benzalkonium chloride; benzethonium chloride; trimethyl tetradecyl ammonium bromide (cetrimide); and cyclodextrins and their adducts, in an amount from about 1% to about 10% by weight of the shell. Charge control agents often cause an unpleasant taste sensation, and additionally may disadvantageously increase oxidation of the shell in which they are employed.

Other limitations shared by conventional encapsulation and enrobing processes include high cost and complexity, limitations on the thickness of the coating or shell, and the creation of raised seams between capsule halves and/or coatings. It would therefore be desirable to have dosage forms of the present invention, which have enhanced versatility for a number of applications, including dosage forms to deliver pharmaceuticals, nutritionals and/or confections, which may be in the form of geltabs or gelcaps, coated tablets, high potency dosage forms and the like. Moreover, such dosage forms have unique and pleasant aesthetic qualities that are valuable in the marketplace.

It is known to produce coatings on tablets by compression, to produce either multiple stacked layers, or core and shell configurations. Such coatings may have shapes which are substantially independent of the shape of the core, as disclosed for example in WO 00/18447. Commercially available compression coating machines are available for example from Korsch America Inc. (a subsidiary of Korsch AG), and described in WO 89/11968. Modified release dosage forms prepared via compression are exemplified in U.S. Pat. Nos. 5,738,874 and 6,294,200, and WO 99/51209. It is possible via compression-coating to produce a 2-portion shell, which may function as a barrier, or release delaying coating, however compression-coated systems are limited by the shell thickness and shell composition as well as processing costs. Gunsel et al., "Compression-coated and layer tablets" in *Pharmaceutical Dosage Forms—Tablets*, edited by H. A. Lieberman, L. Lachman, J. B. Schwartz (2nd ed., rev. and expanded Marcel Dekker, Inc.) pp. 247-284, for example, discloses the thickness of compression coated shells is typically between 800 and 1200 microns. Additionally these authors note that "the advent of film coating dissipated much of the advantage of dry coating since larger quantities of tablets can be coated in a short time with film-formers dissolved in organic or aqueous solvents." Typically, compressed coatings must contain a substantial amount of a compressible material. The compressed shell of WO 00/18447, for example, employs microcrystalline cellulose at a level of about 30%.

Dosage forms having two or more distinct portions are useful in the pharmaceutical arts for overcoming a number of commonly encountered challenges, including the separation of incompatible active ingredients, achieving acceptable content uniformity of a low-dose/high potency active ingredient, delivering one or more active ingredients in a pulsatile manner, and providing unique aesthetic characteristics for dosage form identification. Known methods for achieving a multi-portion pharmaceutical dosage form include particle coating, multi-layer tablets, compression-coating, and spray coating techniques. It is also known for example in the household products industry to assemble solid forms from two or more different parts for the purpose of separating active ingredients, or delivering different active ingredients at different times.

Dosage forms comprising coated particles are described for example in U.S. Pat. No. 5,593,696, which describes oral dosage forms for treating of gastric disorders. The dosage forms contain, as active ingredients, famotidine and sucralfate. In the dosage form, the famotidine is present in the composition in particulate (granulate) form, and the particulate famotidine is provided with a protective barrier layer which prevents interaction between the famotidine and the sucralfate in the composition. The barrier layer is preferably a polymeric coat which dissolves partially in vivo in the stomach environs to release the coated famotidine. U.S. Pat.

No. 5,980,944 describes a solid oral dosage form for the treatment of gastrointestinal disorders comprising a therapeutically effective amount of a pharmaceutical suitable for the treatment of gastric disorders selected from the group consisting of granules of diphenoxylate, loperamide, loperamide-N-oxide, pharmaceutically acceptable salts thereof and combinations thereof, and a therapeutically effective amount of simethicone wherein the pharmaceutical and simethicone are separated by a barrier coat on the granules which is substantially impermeable to simethicone.

Multi-layer tablets are described, for example, in U.S. Pat. No. 5,200,193, which describes multi-layered pharmaceutical active tablets comprising an immediate release layer and a homogeneous compressed sustained release layer comprising an erosion promoter, which upon administration results in a long-lasting, slow and relatively regular incremental release of the pharmaceutical active ingredient. U.S. Pat. No. 6,372,252 describes a pharmaceutical sustained release formulation capable of providing therapeutically effective bioavailability of guaifenesin for at least twelve hours after dosing in a human subject. The modified release guaifenesin bi-layer tablet disclosed has a first portion comprising an immediate release formulation of guaifenesin and a second portion comprising a sustained release formulation of guaifenesin. U.S. Pat. No. 4,999,226 discloses a multi-layered tablet containing an ibuprofen layer, a piperidino-alkanol antihistamine layer, and a layer or layers containing conventional pharmaceutical excipients which is interspersed between the ibuprofen and piperidino-alkanol layer and serves to physically separate them. This multi-layered tablet solves the problems associated with the physical and chemical incompatibilities between ibuprofen and the piperidinoalkanol antihistamines. U.S. Pat. No. 4,198,390 describes a tablet containing at least two separate and discrete volume portions, one of which contains simethicone and the other of which contains antacid. A barrier separates the two volume portions to maintain the simethicone out of contact with the antacid and to prevent migration of the simethicone from its volume portion of the tablet into the volume portion containing the antacid, and vice versa. U.S. Pat. No. 5,133,892 describes a multilayer detergent tablet containing an outer layer, a barrier layer and an inner layer. The tablet sequentially releases ingredients contained in the outer layer and ingredients contained in the inner layer. The time interval between the release of the outer layer ingredients and the release of the inner layer ingredients is controlled by the particular choice of an ingredient for the barrier layer and the relative thicknesses of the inner layer, the barrier layer and the outer layer. The tablet is able to separate in time the dissolution of incompatible ingredients such as an enzyme and a chlorine bleach. The tablet also provides sequential release of a dishwashing composition and a rinse aid composition such that cleaning is accomplished prior to the release of the rinse aid.

Compression-coated tablets are useful for separation of incompatible active ingredients, and for pulsatile release of one or more active ingredients. Compressed coatings may have shapes which are substantially independent of the shape of the core, as disclosed for example in WO 00/18447. Commercially available compression coating machines are available for example from Korsch America Inc., a subsidiary of Korsch AG, and described in WO 89/11968. Modified release dosage forms prepared via compression are exemplified in U.S. Pat. Nos. 5,738,874 and 6,294,200, and WO 99/51209. It is possible, via compression-coating, to produce a 2-portion shell, which may function as a barrier, or release delaying coating; however compression-coated systems are limited by the shell thickness and shell composition as well as processing costs. Gunsel et al., "Compression-Coated and Layer Tablets" in *Pharmaceutical Dosage Forms—Tablets*, edited by H. A. Lieberman, L. Lachman, J. B. Schwartz (2nd ed., rev. and expanded Marcel Dekker, Inc.) pp. 247-284, for example, discloses the thickness of compression coated shells is typically between 800 and 1200 microns. Additionally these authors note that "the advent of film coating dissipated much of the advantage of dry coating since larger quantities of tablets can be coated in a short time with film-formers dissolved in organic or aqueous solvents." Typically, compressed coatings must contain a substantial amount of a compressible material. The compressed shell of WO 00/18447, for example, employs microcrystalline cellulose at a level of about 30%.

One method for addressing the challenge of low-dose/high potency actives is described for example in U.S. Pat. No. 4,322,449 and U.S. Pat. No. RE 31764, which disclose a method for the preparation of pharmaceuticals which comprises using a piezoelectric dosing system to dot liquid, dissolved or suspended active substance onto a pharmaceutical carrier. The disclosed method enables precise dosing of active pharmaceutical ingredients onto pharmaceutical carriers. The dotting is effected by, for example, use of tubular or plate-shaped piezoelectric dosing systems. However, the liquid, dissolved or suspended active substance can also be divided into discrete droplets of specific volume after application of a high pressure during passage through a narrow nozzle, whereby the individual droplets are successively charged electrically and are intermittently deflected electrostatically towards the pharmaceutical carriers.

The incorporation of molded portions into delivery systems has been used in the household products industry to achieve an additional degree of versatility. Assembled forms comprising a mixture of compressed and molded portions are known for example for delivery of detergents. WO 01/49815 describes a composition for use in a dishwasher characterized by a base composition in the form of a tablet which becomes active substantially during the main wash cycle, and at least one separate zone in or on the tablet is provided with a substance that becomes active substantially during the rinse cycle of the dishwasher. One example of such assembled forms comprises a compressed tablet portion having a hemispherical indentation in a major face, and a molded spherical portion fit into and adhered to the indentation in the compressed portion. One limitation of such assemblies is the propensity for the two portions to become detached due to inadequate adherance and minimal surface area of contact between them. In such assemblies, the molded portion may be smaller than the indentation in the compressed portion, e.g. the diameter of the molded portion is at least about 20 microns less that the diameter of the opening in the compressed portion. Alternatively, similar forms may be assembled by press-fitting. In these forms the dimensions of the molded portion and the opening in the compressed portion may be similar. Such assemblies are additionally limited in the types of geometries that are possible at the interface. In press-fit assemblies, the width of the molded portion at the deepest part of the interface may not be substantially larger than the width of the opening through which it must be fit. In other words the draft angle between the outer and inner surfaces of the compressed portion may not be negative. Moreover, the interface or area of contact between the two portions may not form an interlock.

Another significant opportunity in designing pharmaceutical dosage forms is that of product identification and differentiation. It is useful, both from a consumer safety perspective, and a commercial perspective, to have a dosage form with a unique appearance that is readily recognizable and identifiable.

Current techniques for providing unique dosage form identification include the use of intagliations. Intagliations are impressed marks typically achieved by engraving or impressing of a graphical representation, for example a figure, mark, character, symbol such as a letter, a name, a logo, a pictoral representation, and the like, or any combination thereof, in a tablet or other solid dosage form, preferably by a punching procedure. U.S. Pat. No. 5,827,535, for example, describes soft gelatin capsules having an external surface having defined thereon an impressed graphical representation. U.S. Pat. No. 5,405,642 discloses a method of highlighting intagliations in white or colored coated tablets by spraying onto said tablets a suspension comprising a filling material having a different color, a waxy material and a solvent, and removing the solvent and the excess of filling material and waxy material. The suspension of U.S. Pat. No. 5,405,642 comprises a waxy material and a filling material in a critical weight ratio from about 1:3 to about 1:12. Too little waxy material will lead to insufficient bonding of the filling material; too much waxy material the filling material will bond too strongly to the tablet surface and consequently will be difficult to remove afterwards. Suitable solvents for the suspension of U.S. Pat. No. 5,405,642 are those solvents wherein the filling material and, if present, the dye, do not dissolve. For example, non-dyed starches and celluloses may be suspended in alcohols, e.g. ethanol, isopropanol and the like, halogenated hydrocarbons, e.g. dichloromethane, trichloromethane and the like.

EP 060,023 discloses a method of emphasizing intagliations in colored (i.e. not white) solid articles, in particular tablets, by coating the tablet surface and filling up the intagliations with a coating film comprising an optically anisotropic substance. An optical contrast between the tablet surface and the intagliations is obtained, presumably due to the different orientation of the optically anisotropic substance on the tablet surface and in the intagliations. The technique is limited to colored articles and only allows the use of optically anisotropic filling materials. The optical effect merely being based on a different contrast is not particularly clear.

EP 088,556 relates to a method of highlighting intagliations in white or colored tablets by contacting said tablets with a dry, powdery material having a different color than the tablet surface and then removing the excess powdery material not deposited in the intagliations. The powdery material is thought to adhere better to the intagliations of coated tablets than to those of uncoated tablets. Adherence can further be increased by using a mixture of a wax and a powdery material as the deposition material and heating the filled tablets to 40° C.-90° C. to melt the wax. Finally, an outer coating may be applied to the filled tablets. However, the method disclosed in EP 088,556 has several problems. First, it has been found that the adhesion of the powdery material to the intagliations is not satisfactory as the material shows a tendency to loosen and fall out. This problem arises particularly when an outer coating film is applied to the filled tablet and the loosened material becomes fixed in the outer coating film, thus yielding speckled tablets. Addition of a wax to the powdery material to improve adhesion, on the other hand, adversely affects the distribution of the powdery material in that more of it sticks to the surface of the tablet and is difficult to remove. Several other drawbacks are associated with the use of a wax in the dry powdery material. In particular the necessity to heat the tablets filled with a wax and a powdery material to melt the wax poses a barely acceptable risk since many medicines are thermolabile and might deteriorate significantly in the process. Further, it is difficult to evenly dye a dry mixture of a wax and a powdery material, which in turn puts a limitation on the effectively possible color combinations.

U.S. Pat. No. 4,139,589 describes a process for the manufacture of an inlaid tablet, comprising the steps of incorporating into a plastic chewing gum mass a sustained-release active ingredient; incorporating into a non-plastic tablet mass a substantially immediate-release pharmaceutically active ingredient; and respectively converting the chewing gum mass and the tablet mass into the core and the outer layer of the inlaid tablet. A preferred embodiment includes converting the tablet mass into a recessed preformed element, converting the chewing gum mass into the core, inserting the core into the recess of the preformed element, introducing the preformed element and the core into a tablet mold, and subjecting the preformed element and the core in the mold to pressure.

All of the methods described above for producing a dosage form having one or more separate portions are relatively costly, complex, and time-intensive. Additionally, known methods for producing filled-in intagliations are limited in terms of suitable materials and the obtainable surface configurations and appearance of the resultant dosage form. Besides the above-mentioned limitations on the fill material itself, the tablet subcoating must be non-adhesive enough for the fill-in material to rub off upon tumbling in a hot coating pan. These methods cannot produce filled-in intagliations having the fill material raised above the tablet surface, or even perfectly flush with the tablet surface. The prior art product can only have a fill-in material surface that is slightly depressed, abraded, or concave with respect to the tablet surface.

Another significant challenge in the pharmaceutical industry is the opportunity to minimize manufacturing and packaging costs through standardization. Many drugs are available in several different strength tablets for convenience of dosing different patients with varying needs. Typically, higher strength tablets have greater weight and larger size than tablets having lower amounts of active ingredient. Handling and packaging costs could be reduced by having a dosage form design with the versatility to accommodate multiple different dosage amounts of medication in the same size tablet, yet be readily identifiable to patients and healthcare professionals in terms of identity and strength.

Accordingly, it is one object of this invention to provide a composite form comprising at least one active ingredient, a first portion and a second molded portion comprising a second material, in which the second material is inlaid and compositionally different than the first material.

Other objects, features and advantages of this invention will be apparent to those skilled in the art from the detailed description of the invention provided herein.

SUMMARY OF THE INVENTION

In one embodiment, the dosage form of this invention comprises at least one active ingredient, a first portion which comprises an exterior surface and one or more cavities defining at least one interior surface having indentations, and an exterior surface, and a second molded portion which is inlaid into the cavities of the first portion and has an exterior surface. The first and second portions are in contact at an interface, the second portion comprises a solidified thermoplastic material, and the second portion resides substantially conformally upon the indentations.

In another embodiment, the second molded portion is substantially free of pores having a diameter of 0.5 to 5.0 microns.

In another embodiment, the first and second portions are in intimate contact at the interface.

In another embodiment, the first portion is a compressed tablet.

In another embodiment, the first portion is a molded tablet.

In another embodiment, the first portion comprises an intagliation and the second portion resides in the intagliation.

In another embodiment, the exterior surface of the second portion is flush with the exterior surface of the first portion.

In another embodiment, the exterior surface of the second portion is raised with respect to the exterior surface of the first portion.

In another embodiment, the first portion consists essentially of a single homogeneous layer.

In another embodiment, the second molded portion comprises at least one active ingredient.

In another embodiment, the first portion has a first color and the inlaid second portion has a second color.

In another embodiment, the first portion comprises a first active ingredient and the inlaid second portion comprises a second active ingredient which may be the same or different than the first active ingredient.

In another embodiment, the first and second portions together provide a prearranged pattern.

In another embodiment, the first portion comprises a microelectronic device.

In another embodiment, the interior surface of one or more cavities in the first portion has a draft angle having a value less than zero.

In another embodiment, the interface is substantially coextensive with the interior surface.

In another embodiment, the first portion is discontinuous and the second portion is continuous.

In another embodiment of this invention, the dosage form comprises at least one active ingredient, a core having an outer surface and a shell residing on at least a portion of the core outer surface. The shell comprises a first shell portion and a second shell portion, and the second molded shell portion which is inlaid into the first shell portion, and the first and second shell portions are in contact at an interface.

In another embodiment, the shell has an outer surface and the second molded shell portion extends from the outer surface of the core to the outer surface of the shell.

In another embodiment, the first and second shell portions are both discontinuous.

In another embodiment, the first shell portion is discontinuous, and the second shell portion is continuous.

In another embodiment, the first shell portion has a first color and the second shell portion has a second color.

In another embodiment, the core comprises a compressed powder.

In another embodiment, the core comprises an insert.

In another embodiment, the insert comprises an active ingredient.

In another embodiment, one or more of the core, the inlaid portion or the insert comprise an active ingredient.

In another embodiment, the core comprises a microelectronic device.

In another embodiment, the insert comprises a microelectronic device.

In another embodiment, either the first shell portion, second shell portion, or both have a textured outer surface.

In another embodiment, the outer surface of the shell contains a prearranged pattern.

In another embodiment, the shell comprises one or more openings therein.

In another embodiment, the outer surface of the shell is substantially smooth.

In another embodiment, the shell contains indentations, letters, symbols or a pattern.

In another embodiment, the first shell portion contains indentations, letters, symbols or a pattern.

In another embodiment, the second shell portion contains indentations, letters, symbols or a pattern.

In another embodiment, the first shell portion, second shell portion or both contain raised protrusions in the form of letters, symbols or a pattern.

In another embodiment, the inlaid portion is substantially free of pores having a diameter of 0.5-5.0 microns.

In another embodiment, the second shell portion has a portion thereof having a draft angle having a value less than zero at the interface.

In another embodiment of this invention, the dosage form comprises at least one active ingredient, a core, and a shell having a first molded shell portion which is discontinuous, and a second molded shell portion which is continuous, such that the discontinuities of the first shell portion are due to the presence of the second molded shell portion, and the first and second shell portions are compositionally different.

In another embodiment, the first and second shell portions comprise a solidified thermoplastic material.

In another embodiment, the exterior surfaces of the first and second shell portions are colinear.

In another embodiment, the second molded portion has a portion thereof having a draft angle having a value less than zero.

In another embodiment, the cavities define a plurality of side walls for receiving the inlaid portion, and the side walls have a draft angle having a value less than zero.

In another embodiment, either the first portion, the second portion, or both contain an active ingredient.

DETAILED DESCRIPTION OF THE INVENTION

Figure 1A:
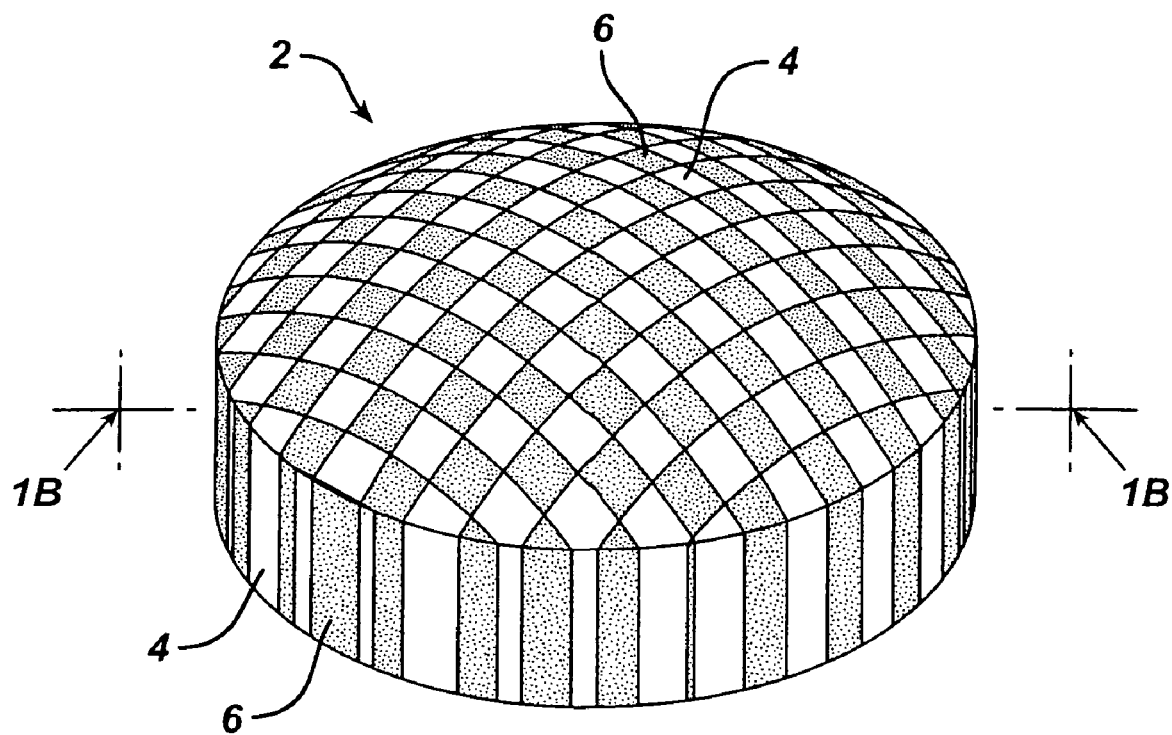
FIGS. 1A and 1B depict an example of a dosage form of this invention.

In one embodiment of this invention, the dosage form comprises at least one active ingredient, a first portion which comprises one or more cavities and indentations and an exterior surface, and a second molded portion which is inlaid into the cavities of the first portion and has an exterior surface. The first and second portions are in contact at an interface, the second portion comprises a solidified thermoplastic material, and the second portion resides substantially conformally upon the indentations of the first portion.

As used herein, an "exterior surface" of a portion is a surface that comprises part of the exterior surface of the finished dosage form.

As used herein, the term "substantially conformally" refers to the fact that the cavities of the first portion are defined by surfaces having peaks and valleys therein, and the second portion resides in the cavities and the second portion also has peaks and valleys in its surfaces, such that the peaks and valleys of the surfaces of the second portion correspond substantially inversely to the major peaks and valleys of the surfaces defined by the cavities.

In another embodiment of this invention, the dosage form comprises at least one active ingredient, a core having an outer surface and a shell residing on at least a portion of the core outer surface, wherein the shell comprises a first shell portion and a second shell portion, and the second molded shell portion which is inlaid into the first shell portion.

In another embodiment of this invention, the dosage form comprises at least one active ingredient, a core, and a shell having a first molded shell portion which is discontinuous, and a second molded shell portion which is continuous, such that the discontinuities of the first shell portion are due to the presence of the second molded shell portion, and the first and second shell portions are compositionally different.

As used herein, the term "compositionally different" means having features that are readily distinguishable by qualitative or quantitative chemical analysis, physical testing, or visual observation. For example, the first and second materials may contain different ingredients, or different levels of the same ingredients, or the first and second materials may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In certain embodiments the first portion consists essentially of a single homogeneous layer. In other words, it may be a single molded composition or a single compressed tablet. If the portion were divided into parts, each part would have the same density, porosity, color, crystallinity, etc.

As used herein, the term "dosage form" applies to any solid object, semi-solid, or liquid composition, designed to contain a specific pre-determined amount (i.e. dose) of a certain ingredient, for example an active ingredient as defined below. Suitable dosage forms may be pharmaceutical drug delivery systems, including those for oral administration, buccal administration, rectal administration, topical, transdermal, or mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human. In another preferred embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof, H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment of the invention, the active agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active agent is selected from analgesics, anti-inflammatories, and antipyretics: e.g. non-steroidal anti-inflammatory drugs (NSAIDs), including propionic acid derivatives: e.g. ibuprofen, naproxen, ketoprofen and the like; acetic acid derivatives: e.g. indomethacin, diclofenac, sulindac, tolmetin, and the like; fenamic acid derivatives: e.g. mefanamic acid, meclofenamic acid, flufenamic acid, and the like; biphenylcarbodylic acid derivatives: e.g. diflunisal, flufenisal, and the like; and oxicams: e.g. piroxicam, sudoxicam, isoxicam, meloxicam, and the like. In a particularly preferred embodiment, the active agent is selected from propionic acid derivative NSAID: e.g. ibuprofen, naproxen, flurbiprofen, fenbufen, fenoprofen, indoprofen, ketoprofen, fluprofen, pirprofen, carprofen, oxaprozin, pranoprofen, suprofen, and pharmaceutically acceptable salts, derivatives, and combinations thereof. In another embodiment of the invention, the active agent may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active agent may be selected from pseudoephedrine, phenylpropanolamine, chlorpheniramine, dextromethorphan, diphenhydramine, astemizole, terfenadine, fexofenadine, loratadine, desloratidine, doxilamine, norastemizole, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art. In one embodiment, the dosage form comprises at least about 85 weight percent of the active ingredient.

In certain embodiments in which modified release of the active ingredient is desired, the active ingredient may optionally be coated with a release-modifying coating, as are well known in the art. This advantageously provides an additional tool for modifying the release profile of active ingredient from the dosage form. For example, the dosage form may contain coated particles of one or more active ingredients, in which the particle coating confers a release modifying function, as is well known in the art. Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release active ingredients may also be employed. For example, acetaminophen particles which are encapsulated with release-modifying polymers by a coaccervation process may be used in the present invention. Coaccervation-encapsulated acetaminophen may be purchased commercially from Eurand America, Inc. (Vandalia, Ohio) or from Circa Inc. (Dayton, Ohio).

If the active ingredient has an objectionable taste, and the dosage form is intended to be chewed or disintegrated in the mouth prior to swallowing, the active ingredient may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. (Vandalia, Ohio), or from Circa Inc. (Dayton, Ohio).

In embodiments in which the first portion is prepared via compression, suitable excipients include fillers, binders, disintegrants, lubricants, glidants, and the like.

In embodiments in which the first portion is prepared via compression, suitable fillers include water-soluble compressible carbohydrates such as sugars, which include dextrose, sucrose, isomaltalose, fructose, maltose, and lactose, polydextrose, sugar-alcohols, which include mannitol, sorbitol, isomalt, maltitol, xylitol, erythritol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

In embodiments in which the first portion is prepared via compression, suitable binders include dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof.

In embodiments in which the first portion is prepared via compression, suitable disintegrants include sodium starch glycolate, cross-linked polyvinylpyrrolidone, cross-linked carboxymethylcellulose, starches, microcrystalline cellulose, and the like.

In embodiments in which the first portion is prepared via compression, suitable lubricants include long chain fatty acids and their salts, such as magnesium stearate and stearic acid, talc, and waxes.

In embodiments in which the first portion is prepared via compression, suitable glidants include colloidal silicon dioxide, and the like.

In embodiments in which the first portion is prepared via compression, the dosage form of the invention may also incorporate pharmaceutically acceptable adjuvants, including, for example, preservatives, high intensity sweeteners such as aspartame, acesulfame potassium, cyclamate, saccharin, sucralose, and the like; and other sweeteners such as dihydroalcones, glycyrrhizin, Monellin™, stevioside, Talin™, and the like; flavors, antioxidants, surfactants, and coloring agents.

The active ingredient or ingredients are preferably capable of dissolution upon contact with a fluid such as water, stomach acid, intestinal fluid or the like. In a preferred embodiment the dissolution characteristics of the active ingredient meet USP specifications for immediate release tablets containing the active ingredient. In embodiments in which it is desired for the active ingredient to be absorbed into the systemic circulation of an animal, the active ingredient or ingredients are preferably capable of dissolution upon contact with a fluid such as water, gastric fluid, intestinal fluid or the like. In one embodiment, the dissolution characteristics of the active ingredient meet USP specifications for immediate release tablets containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the active ingredient are modified: e.g. controlled, sustained, extended, retarded, prolonged, delayed and the like.

Figure 1B:
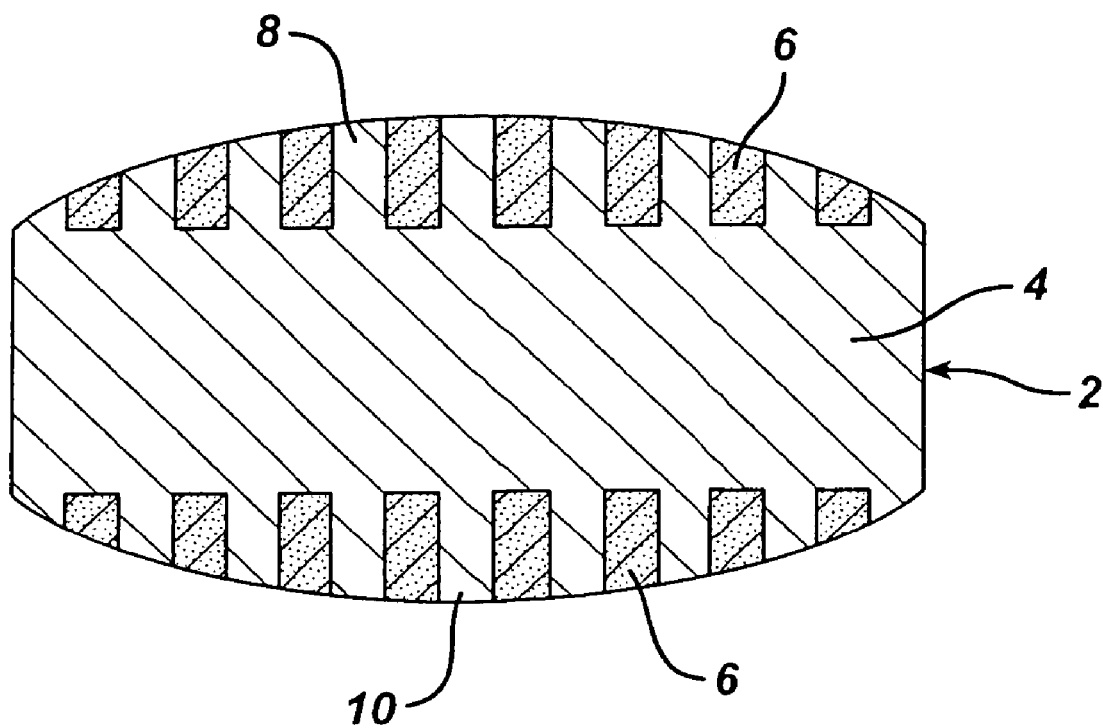

An overall understanding of the dosage form of this invention may be obtained by reference to FIGS. 1A, 1B, 2A and 2B. FIGS. 1A and 1B depict one embodiment of the dosage form of this invention. In FIG. 1A, a dosage form 2 is depicted which comprises a first portion 4. The first portion comprises a plurality of debossments which in turn comprise inlaid second portions 6. In this embodiment, a first active ingredient is located within first portion 4 and a second active ingredient is located within inlaid second portions 6. FIG. 1B is a cross-sectional view of the dosage form 2 of FIG. 1A. As shown in FIG. 1B, in this embodiment molded inlaid second portions 6 extend partially into the first portion 4 from both first surface 8 and second surface 10. In this embodiment a first active ingredient is located within inlaid second portions 6 and a second active ingredient (which may be the same or different than the first active ingredient) is located within first portion 4, although in other embodiments only one of inlaid second portions 6 or first portion 4 may contain an active ingredient.

In other embodiments as depicted in FIGS. 1A and 1B, a clear or semi-transparent coating may reside on first surface 8 and second surface 10.

Figure 2A:
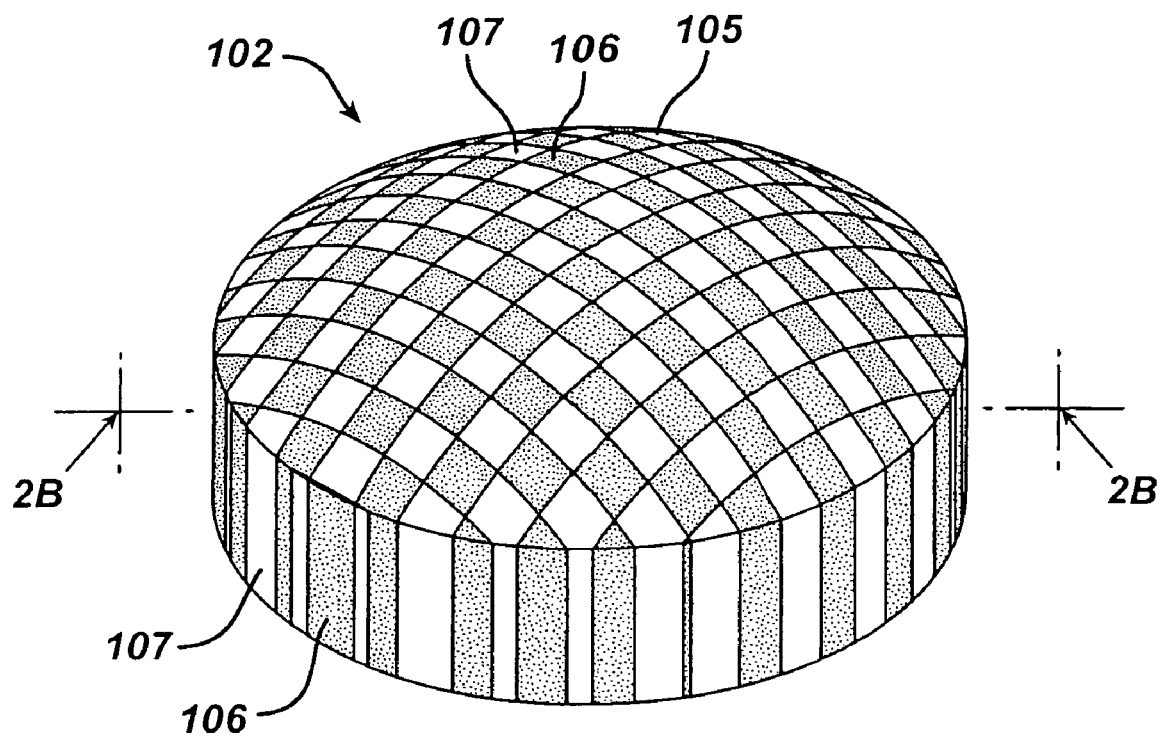
FIGS. 2A and 2B depict another example of a dosage form of this invention, in which the core has a shell residing thereon which contains an inlaid portion.
Figure 2B:
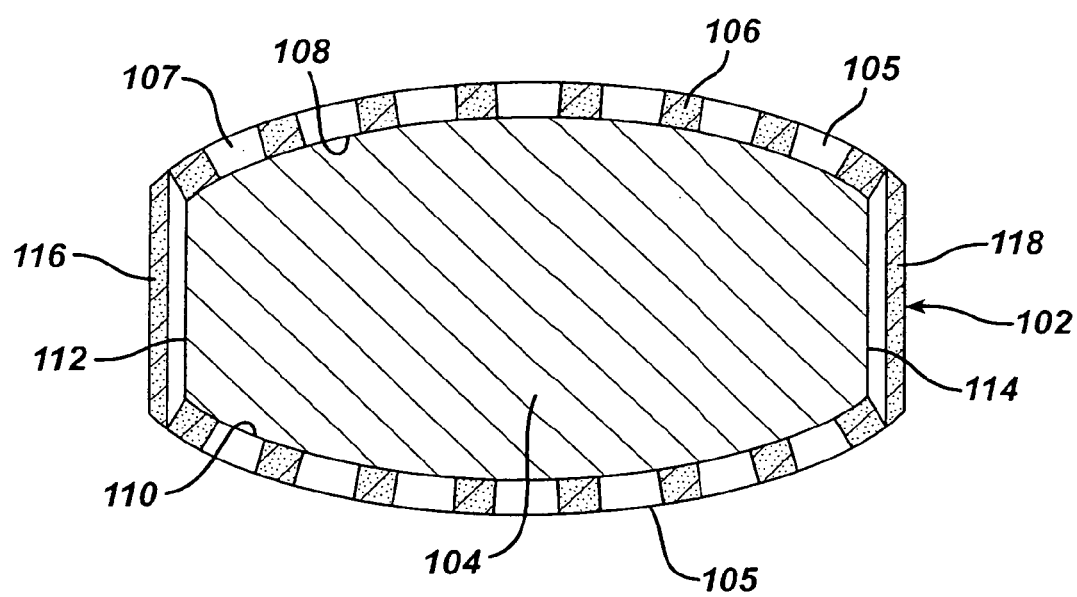

FIGS. 2A and 2B depict another embodiment of this invention. FIG. 2A depicts a dosage form 102 which comprises a core 104. The core has a shell 105 residing on at least a portion of the exterior surface of core 104. The shell 105 is shown in greater detail in FIG. 2B, which is a cross-sectional view of the dosage form of FIG. 2A. As shown in FIG. 2B, the shell 105 residing on the exterior surfaces 108 and 110 of core 104 comprises a first shell portion 107 having cavities, with molded inlaid second shell portions 106 residing in the cavities. In this embodiment, a first active ingredient is located within shell portion 107 and a second active ingredient is located within inlaid second shell portions 106, although in other embodiments only one of first shell portion 107 or inlaid second shell portions 106 may contain an active ingredient. Core 104 may optionally also contain an active ingredient, which may be the same or different than the active ingredient contained in first shell portion 107 and inlaid second shell portions 106. As depicted in FIG. 2B, the shell 105 may extend along the side portions 112 and 114 of core 104, and inlaid portions 116 and 118 may reside in the indentations of shell 105. In this embodiment, the cavities extend through the first shell portion up to the surface of the core; however, in other embodiments the cavities may only extend through a part of the first shell portion.

The core (or substrate) may be any solid or semi-solid form. The core may prepared by any suitable method, for example the core be a compressed dosage form, or may be molded. As used herein, "substrate" refers to a surface or underlying support, upon which another substance resides or acts, and "core" refers to a material which is at least partially enveloped or surrounded by another material. For the purposes of the present invention, the terms may be used interchangeably: i.e. the term "core" may also be used to refer to a "substrate." Preferably, the core comprises a solid, for example, the core may be a compressed or molded tablet, hard or soft capsule, suppository, or a confectionery form such as a lozenge, nougat, caramel, fondant, or fat based composition. In certain other embodiments, the core may be in the form of a semi-solid or a liquid in the finished dosage form.

The core may be in a variety of different shapes. For example, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, sphere, torus, or the like. Exemplary core shapes which may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

1. Shallow Concave.
2. Standard Concave.
3. Deep Concave.
4. Extra Deep Concave.
5. Modified Ball Concave.
6. Standard Concave Bisect.
7. Standard Concave Double Bisect.
8. Standard Concave European Bisect.
9. Standard Concave Partial Bisect.
10. Double Radius.
11. Bevel & Concave.
12. Flat Plain.
13. Flat-Faced-Beveled Edge (F.F.B.E.).
14. F.F.B.E. Bisect.
15. F.F.B.E. Double Bisect.
16. Ring.
17. Dimple.
18. Ellipse.
19. Oval.
20. Capsule.
21. Rectangle.
22. Square.
23. Triangle.
24. Hexagon.
25. Pentagon.
26. Octagon.
27. Diamond.
28. Arrowhead.
29. Bullet.
30. Barrel.
31. Half Moon.
32. Shield.
33. Heart.
34. Almond.
35. House/Home Plate.
36. Parallelogram.
37. Trapezoid.
38. FIG. 8/Bar Bell.
39. Bow Tie.
40. Uneven Triangle.

The core or sub-core may optionally be at least partially covered by a compressed, molded, or sprayed sub-coating. However, in one preferred embodiment, the core may be substantially free of the subcoating: i.e. there is no subcoating located between the outer surface of the core and the inner surface of the shell.

In another embodiment of this invention, the core is a compressed dosage form: i.e. a tablet, obtained from a compressed powder. The powder may preferably comprise an active ingredient, and optionally comprise various excipients, such as binders, disintegrants, lubricants, fillers and the like, as is conventional, or the powder may comprise other particulate material of a medicinal or non-medicinal nature, such as inactive placebo blends for tableting, confectionery blends, and the like. One particular formulation comprises active ingredient, powdered wax (such as shellac wax, microcrystalline wax, polyethylene glycol, and the like), and optionally disintegrants and lubricants and is described in more detail at pages 4-11 of pending U.S. patent application Ser. No. 09/966,493, the disclosure of which is incorporated herein by reference.

The core may optionally comprise a sub-core (which may also be referred to as an "insert"), which may be made by any method, for example compression or molding, and which may optionally contain one or more active ingredients.

In one embodiment of the invention, the dosage forms of this invention comprise a core made from a blend of powders having an average particle size of about 50 to about 500 microns. In one embodiment, the active ingredient has an average particle size of about 50 to about 500 microns. In another embodiment, at least one excipient has an average particle size of about 50 to about 500 microns, e.g. about 100 to about 500 microns. In one such embodiment, a major excipient, i.e. and excipient comprising at least 50% by weight of the core, has an average particle size of about 50 to about 500 microns, e.g. about 100 to about 500 microns. Particles in this size range are particularly useful for direct compression processes. In a preferred embodiment of the invention, the core may be prepared by a direct compression process.

In one such embodiment of the invention, the core is a directly compressed tablet, made from a powder which is substantially free of water soluble polymeric binders and hydrated polymers. This composition is advantageous for maintaining an immediate release dissolution profile, minimizing processing and material costs, and providing for optimal physical and chemical stability of the dosage form.

In embodiments in which the core is prepared by direct compression, the materials comprising the core, e.g. the active ingredient or ingredients and excipients, are blended together, preferably as dry powders, and fed into an apparatus that applies pressure and forms a core. Any suitable compacting apparatus may be used, including for example a roller compactor such as a chilsonator or drop roller; or a conventional tablet press. Preferably, the core is formed by compaction using a rotary tablet press as known in the art. In a rotary tablet press, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch. The direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which can have an adverse effect on dissolution.

In a preferred embodiment, the core is prepared by the compression methods and apparatus described in copending U.S. application Ser. No. 09/966,509, pages 16-27, the disclosure of which is incorporated herein by reference. Specifically, the core is made using a rotary compression module comprising a fill zone, insertion zone, compression zone, ejection zone, and purge zone in a single apparatus having a double row die construction as shown in FIG. 6 of U.S. application Ser. No. 09/966,509. The dies of the compression module are preferably filled using the assistance of a vacuum, with filters located in or near each die. The purge zone of the compression module includes an optional powder recovery system to recover excess powder from the filters and return the powder to the dies.

In another embodiment, the core is prepared by a wet-granulation method, in which the active ingredient or ingredients, appropriate excipients, and a solution or dispersion of a wet binder (e.g. an aqueous cooked starch paste, or solution of polyvinyl pyrrolidone) are mixed and granulated. Suitable apparatuses for wet granulation include low shear, e.g. planetary mixers, high shear mixers, and fluid beds, including rotary fluid beds. The resulting granulated material is dried, and optionally dry-blended with further ingredients, e.g. adjuvants and/or excipients such as for example lubricants, colorants, and the like. The final dry blend is then suitable for compression by the methods described in the previous paragraph.

Methods for direct compression and wet granulation processes are known in the art, and are described in detail in, for example, Lachman, et al., *The Theory and Practice of Industrial Pharmacy*, Chapter 11 (3rd ed. 1986).

In one embodiment, the first portion or core is prepared by thermal setting molding using the method and apparatus described in copending U.S. patent application Ser. No. 09/966,450, pages 57-63, the disclosure of which is incorporated herein by reference. In this embodiment, the first portion or core is formed by injecting a starting material in flowable form into a molding chamber. The starting material preferably comprises an active ingredient and a thermal setting material at a temperature above the melting point of the thermal setting material but below the decomposition temperature of the active ingredient. The starting material is cooled and solidifies in the molding chamber into a shaped form (i.e. having the shape of the mold).

In another embodiment, the first portion or core is prepared by thermal cycle molding using the method and apparatus described in copending U.S. patent application Ser. No. 09/966,497, pages 27-51, the disclosure of which is incorporated herein by reference. In this embodiment, the first portion or core is formed by injecting a starting material in flowable form into a heated molding chamber. The starting material preferably comprises an active ingredient and a thermoplastic material at a temperature above the set temperature of the thermoplastic material but below the decomposition temperature of the active ingredient. The starting material is cooled and solidifies in the molding chamber into a shaped form (i.e. having the shape of the mold).

According to this method, the starting material must be in flowable form. For example, it may comprise solid particles suspended in a molten matrix, for example a polymer matrix. The starting material may be completely molten or in the form of a paste. The starting material may comprise an active ingredient dissolved in a molten material. Alternatively, the starting material may be made by dissolving a solid in a solvent, which solvent is then evaporated from the starting material after it has been molded.

The starting material may comprise any edible material which is desirable to incorporate into a shaped form, including active ingredients such as those active ingredients previously described with respect to the core, nutritionals, vitamins, minerals, flavors, sweeteners, and the like. Preferably, the starting material comprises an active ingredient and a thermal setting material. The thermal setting material may be any edible material that is flowable at a temperature between about 37 and about 250° C., and that is a solid or semi-solid at a temperature between about −10° C. and about 35° C. The flowable material may be any edible material that is flowable at a temperature between about 37° C. and 250° C., and that is solid, semi-solid, or can form a gel at a temperature between about −10° C. and about 35° C. When it is in the fluid or flowable state, the flowable material may comprise a dissolved or molten component, and optionally a solvent such as for example water or organic solvents, or combinations thereof. The solvent may be partially or substantially removed by drying. Suitable flowable materials include those comprising thermal setting materials, film forming polymers, gelling polymers, hydrocolloids, low melting hydrophobic materials such as fats and waxes, non-crystallizable carbohydrates, and the like. Preferred thermal setting materials include water-soluble polymers such as polyalkylene glycols, polyethylene oxides and derivatives, and sucrose esters; fats such as cocoa butter, hydrogenated vegetable oil such as palm kernel oil, cottonseed oil, sunflower oil, and soybean oil; free fatty acids and their salts; mono- di- and triglycerides, phospholipids, waxes such as carnuba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; low-moisture polymer solutions such as mixtures of gelatin and other hydrocolloids at water contents up to about 30% such as those used to make "gummi" confection forms. In a particularly preferred embodiment, the thermal setting material is a blend of fats and mono- and diglycerides.

In another embodiment, the core may be a hollow or evacuated core. For example, the core may be an empty capsule shell. Alternatively, a hollow core may be prepared for example by molding. In one such method, flowable material is injected into a mold cavity, the cavity is brought to a temperature at which the outer surface of the core (which is in contact with the mold) begins to solidify or set. The excess flowable material from the center of the core is then withdrawn from the mold using suitable means, for example a piston pump. In another such method, an empty capsule is used as a sub-core, and a coating layer is formed thereon by methods known in the art such as, for example, spray-coating, dip-coating, or thermal cycle molding as described in copending U.S. patent application Ser. No. 09/966,497, pages 27-51, the disclosure of which is incorporated herein by reference.

In certain embodiments of the invention, the core may further comprise a subcoating, applied by any method, for example spraying, compression, or molding. In certain other embodiments of the invention, the core may be substantially free of a subcoating.

In another embodiment of the invention, the core contains at least in part one or more inserts. The inserts can be made in any shape or size. For instance, irregularly shaped inserts can be made, that is shapes having no more than one axis of symmetry. Cylindrically shaped inserts may also be made. The insert may be made using conventional techniques such as panning, compression, or molding. In one embodiment, the insert is prepared using the thermal setting method and apparatus as described herein.

In one embodiment of the invention, the insert may have an average diameter from about 100 to about 1000 microns. In another embodiment of this invention, the insert may have an average diameter or thickness from about 10% to about 90% of the diameter or thickness of the core. In yet another embodiment of this invention, the core may comprise a plurality of inserts.

In another embodiment, the insert may have an average diameter, length, or thickness greater than about 90% of the diameter or thickness of the core, for example the insert may have an average length greater than about 100% of the thickness of the core.

In another embodiment of the invention, the core, the insert (if employed), the inlaid portion or any combination thereof may comprise a microelectronic device (e.g. an electronic "chip") which may be used as an active component or to control, for example, the rate of release of active ingredients within the core or insert in response to an input signal. Examples of such microelectronic devices are as follows:

(1) Integrated, self-regulating responsive therapeutic devices including biosensors, electronic feedback and drug/countermeasure release devices which are fully integrated. Such devices eliminate the need for telemetry and human intervention, and are disclosed, for example, at www.chiprx.com/products.html, which is incorporated herein by reference;

(2) Miniaturized diagnostic imaging systems which comprise a swallowable capsule containing a video camera, and are disclosed, for example, at www.givenimaging.com/usa/default.asp, which is incorporated herein by reference;

(3) Subcutaneous glucose monitors which comprise implantable or insertable sensor devices which detect changes in glucose concentration within intestinal fluid, and communicate to an external detector and data storage device. Such devices are disclosed, for example, at www.applied-medical.co.uk/glucose.htm, which is incorporated herein by reference;

(4) Microdisplay vision aid devices encapsulated in an artificial intraocular lens. Such devices include a receiver for power supply, data and clock recovery, and a miniature LED array flip-chip bonded to a silicon CMOS driver circuit and micro optics, and are disclosed, for example, at http://ios.oe.uni-duisberg.de/e/, which is incorporated herein by reference. The microdisplay device receives a bit-stream+energy wireless signal from a high dynamic range CMOS camera placed outside the eye which generates a digital black & white picture which is converted by a digital signal processing unit (DAP) into a serial bit-stream with a data rate of approximately 1 Mbit/s. The image is projected onto the retina;

(5) Microchips used to stimulate damaged retinal cells, allowing them to send visual signals to the brain for patients with macular degeneration or other retinal disorders. The chip is 2 mm×25 microns, and contains approximately 5,000 microscopic solar cells ("microphotodiodes"), each with its own stimulating electrode. These microphotodiodes convert the light energy from images into electrical chemical impulses that stimulate the remaining functional cells of the retina in patients with AMD and RP. Such microchips are disclosed, for example, at www.optobionics.com/artificialretina.htm, which is incorporated herein by reference;

(6) Disposable "smart needles" for breast biopsies which display results in real time. The device fits into a 20 to 21 gauge disposable needle that is connected to a computer, as the needle is inserted into the suspicious lesion. The device measures oxygen partial pressure, electrical impedance, temperature, and light scattering and absorption properties including deoxygenated hemoglobin, vascularization, and tissue density. Because of the accuracy benefits from the six simultaneous measurements, and real-time nature of the device, it is expected to exceed the accuracy levels achieved by the core needle biopsy procedure and approach the high level of accuracy associated with surgical biopsies. Further, if cancer is found, the device can be configured to deliver various therapies such as cancer markers, laser heat, cryogenics, drugs, and radioactive seeds. Such devices are disclosed, for example, at www.bioluminate.com/description.html, which is incorporated herein by reference; and (7) Personal UV-B recorders, which are instrument grade devices for measuring and recording UVB exposure and fit into a wrist-watch face. They may also be worn as a patch.

In one embodiment of the invention, the shell or inlaid portion or both are made from a flowable material.

The inlaid portion must be molded. In a preferred embodiment of the invention, the inlaid portion is prepared using thermal setting molding or thermal cycle molding as described above.

The inlaid portion of the present invention may comprise any material which can be molded, including for example, film formers, low-melting hydrophobic materials, gelling polymers, thickeners, plasticizers, adjuvants, and excipients.

In one embodiment, the inlaid portion preferably comprises at least about 50%, preferably at least about 80%, most preferably at least about 90% of a material selected from film formers, gelling polymers, low-melting hydrophobic materials, non-crystallizable sugars or sugar alcohols, and mixtures thereof. In another embodiment, the inlaid portion comprises at least about 50%, preferably at least about 80%, most preferably at least about 90% of a material selected from film formers, gelling polymers, low-melting hydrophobic materials, and mixtures thereof.

In one embodiment of the invention, the flowable material comprises gelatin as a gelling polymer. Gelatin is a natural, thermogelling polymer. It is a tasteless and colorless mixture of derived proteins of the albuminous class which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10° C. for 17 hours. In a preferred embodiment, the flowable material is an aqueous solution comprising 20% 275 Bloom pork skin gelatin, 20% 250 Bloom Bone Gelatin, and approximately 60% water.

Other preferred flowable materials may comprise sucrose-fatty acid esters; fats such as cocoa butter, hydrogenated vegetable oil such as palm kernel oil, cottonseed oil, sunflower oil, and soybean oil; free fatty acids and their salts; mono- di- and triglycerides, phospholipids, waxes such as carnuba wax, spermaceti wax, beeswax, candelilla wax, shellac wax, microcrystalline wax, and paraffin wax; fat-containing mixtures such as chocolate; sugar in the form on an amorphous glass such as that used to make hard candy forms, sugar in a supersaturated solution such as that used to make fondant forms; carbohydrates such as sugar-alcohols (for example, sorbitol, maltitol, mannitol, xylitol and erythritol), or thermoplastic starch; and low-moisture polymer solutions such as mixtures of gelatin and other hydrocolloids at water contents up to about 30%, such as for example those used to make "gummi" confection forms.

In one embodiment of the invention, the flowable material may comprise a film former such as a cellulose ether, e.g. hydroxypropylmethylcellulose or a modified starch, e.g. waxy maize starch; optionally an extender, such as polycarbohydrates, e.g. maltodextrin; optionally a thickener, such as a hydrocolloid, e.g. xanthan gum or carrageenan, or a sugar, e.g. sucrose; optionally a plasticizer, e.g. polyethylene glycol, propylene glycol, vegetable oils such as castor oil, glycerin, and mixtures thereof.

Any film former known in the art is suitable for use in the flowable material. Examples of suitable film formers include, but are not limited to, polyvinylalcohol (PVA), polyvinylpyrrolidone (PVP), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), methacrylic acid and methacrylate ester copolymers, polyethylene oxide and polyvinylpyrrolidone copolymers, gelatin, proteins such as whey protein, coaggulatable proteins such as albumin, casein, and casein isolates, soy protein and soy protein isolates, pregelatinized starches, and polymers and derivatives and mixtures thereof.

One suitable hydroxypropylmethylcellulose compound is HPMC 2910, which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename METHOCEL E. METHOCEL E5, which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20° C. in a 2% aqueous solution as determined by a Ubbelohde viscometer. As used herein, "degree of substitution" shall mean the average number of substituent groups attached to a anhydroglucose ring, and "hydroxypropyl molar substitution" shall mean the number of moles of hydroxypropyl per mole anhydroglucose.

As used herein, "modified starches" include starches that have been modified by crosslinking, chemically modified for improved stability, or physically modified for improved solubility properties. As used herein, "pre-gelatinized starches" or "instantized starches" refers to modified starches that have been pre-wetted, then dried to enhance their cold-water solubility. Suitable modified starches are commercially available from several suppliers such as, for example, A. E. Staley Manufacturing Company, and National Starch & Chemical Company. One suitable modified starch includes the pre-gelatinized waxy maize derivative starches that are commercially available from National Starch & Chemical Company under the tradenames PURITY GUM and FILMSET, and derivatives, copolymers, and mixtures thereof. Such waxy maize starches typically contain, based upon the total weight of the starch, from about 0 percent to about 18 percent of amylose and from about 100% to about 88% of amylopectin.

Suitable tapioca dextrins include those available from National Starch & Chemical Company under the tradename CRYSTAL GUM or K-4484, and derivatives thereof such as modified food starch derived from tapioca, which is available from National Starch and Chemical under the tradename PURITY GUM 40, and copolymers and mixtures thereof.

Any thickener known in the art is suitable for use in the flowable material. Examples of such thickeners include but are not limited to hydrocolloids (also referred to herein as gelling polymers) such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, and derivatives and mixtures thereof. Additional suitable thickeners include crystallizable carbohydrates, and the like, and derivatives and combinations thereof. Suitable crystallizable carbohydrates include the monosaccharides and the oligosaccharides. Of the monosaccharides, the aldohexoses e.g., the D and L isomers of allose, altrose, glucose, mannose, gulose, idose, galactose, talose, and the ketohexoses e.g., the D and L isomers of fructose and sorbose along with their hydrogenated analogs: e.g., glucitol (sorbitol), and mannitol are preferred. Of the oligosaccharides, the 1,2-disaccharides sucrose and trehalose, the 1,4-disaccharides maltose, lactose, and cellobiose, and the 1,6-disaccharides gentiobiose and melibiose, as well as the trisaccharide raffinose are preferred along with the isomerized form of sucrose known as isomaltulose and its hydrogenated analog isomalt. Other hydrogenated forms of reducing disaccharides (such as maltose and lactose), for example, maltitol and lactitol are also preferred. Additionally, the hydrogenated forms of the aldopentoses: e.g., D and L ribose, arabinose, xylose, and lyxose and the hydrogenated forms of the aldotetroses: e.g., D and L erythrose and threose are preferred and are exemplified by xylitol and erythritol, respectively.

Suitable xanthan gums include those available from C.P. Kelco Company under the tradename KELTROL 1000, XANTROL 180, or K9B310.

Suitable thermoplastic materials can be molded and shaped when heated, and include both water soluble and water insoluble polymers that are generally linear, not crosslinked, nor strongly hydrogen bonded to adjacent polymer chains. Examples of suitable thermoplastic materials include: chemically modified cellulose derivatives such as hydroxypropyl cellulose (HPC), hydroxypropylmethyl cellulose (HPMC), methyl cellulose (MC), cellulose acetate (CA), ethyl cellulose (EC), cellulose acetate butyrate (CAB), cellulose propionate; vinyl polymers such as polyvinyl alcohol (PVA) and polyvinyl pyrrolidone (PVP); thermoplastic starch; natural and chemically modified proteins such as gelatin, soy protein isolates, whey protein, myofibrillar proteins, and the milk derived caseinate proteins; and derivatives and combinations thereof.

Any plasticizer known in the pharmaceutical art is suitable for use in the present invention, and may include, but not be limited to polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof. In solutions containing a cellulose ether film former, an optional plasticizer may be present in an amount, based upon the total weight of the solution, from about 0% to about 40%.

The flowable material may optionally comprise adjuvants or excipients, which may comprise up to about 20% by weight of the flowable material. Examples of suitable adjuvants or excipients include detackifiers, humectants, surfactants, anti-foaming agents, colorants, flavorants, sweeteners, opacifiers, and the like. In one preferred embodiment, the flowable material comprises less than 5% humectants, or alternately is substantially free of humectants, such as glycerin, sorbitol, maltitol, xylitol, or propylene glycol. Humectants have traditionally been included in pre-formed films employed in enrobing processes, such as that disclosed in U.S. Pat. Nos. 5,146,730 and 5,459,983 to ensure adequate flexibility or plasticity and bondability of the film during processing. Humectants function by binding water and retaining it in the film. Pre-formed films used in enrobing processes can typically comprise up to 45% water. Disadvantageously, the presence of humectant prolongs the drying process, and can adversely affect the stability of the finished dosage form.

In a preferred embodiment of the invention, the inlaid portion of the dosage form comprises at least about 80%, preferably at least about 90% of a material selected from film formers, gelling polymers (hydrocolloids), thermoplastic materials, low-melting hydrophobic materials, non-crystallizable sugars, and mixtures thereof. The inlaid portion may be formed by injection molding, advantageously minimizing or eliminating the need for direct-compression filler-binders such as microcrystalline cellulose, spray-dried lactose, mineral salts such as calcium phosphate, crystalline sugars such as sucrose, dextrates and the like. These materials would disadvantageously detract from the clarity and stability of the inlaid portion. Preferably the inlaid portion of the present invention comprises less than about 10%, e.g. less than about 1%, or less than about 0.1% of direct-compression filler-binders. The inlaid portion used in the present invention are thus an improvement over compression-coated shells, which typically comprise at least about 30% of a direct-compression filler-binder. See, for example, WO 00/18447.

The inlaid portion may be prepared by molding, as discussed above.

In one embodiment of the invention, the inlaid portion comprises a modified release composition as described in U.S. patent application Ser. No. 10/476,238, filed Sep. 28, 2002 (corresponding to WO/03026626), the disclosure of which is incorporated herein by reference.

In another embodiment of the invention, the inlaid portion comprises any of the modified release compositions described in U.S. patent application Ser. Nos. 10/477,334, filed Sep. 28, 2002, or 10/476,504, filed Sep. 28, 2010, (corresponding to WO/2003026624 or WO/2003/026615, respectively), the disclosures of which are incorporated herein by reference.

In a preferred embodiment, the inlaid portion is substantially free of pores having a diameter of 0.5-5.0 microns. As used herein, "substantially free" means that the inlaid portion has a pore volume of less than about 0.02 cc/g, preferably less than about 0.01 cc/g, more preferably less than about 0.005 cc/g, in the pore diameter range of 0.5 to 5.0 microns. Typical compressed materials have pore volumes of more than about 0.02 cc/g in this pore diameter range. Pore volume, pore diameter and density may be determined using a Quantachrome Instruments PoreMaster 60 mercury intrusion porosimeter and associated computer software program known as "Porowin." The procedure is documented in the Quantachrome Instruments PoreMaster Operation Manual. The PoreMaster determines both pore volume and pore diameter of a solid or powder by forced intrusion of a non-wetting liquid (mercury), which involves evacuation of the sample in a sample cell (penetrometer), filling the cell with mercury to surround the sample with mercury, applying pressure to the sample cell by: (i) compressed air (up to 50 psi maximum); and (ii) a hydraulic (oil) pressure generator (up to 60000 psi maximum). Intruded volume is measured by a change in the capacitance as mercury moves from outside the sample into its pores under applied pressure. The corresponding pore size diameter (d) at which the intrusion takes place is calculated directly from the so-called "Washburn Equation": $d=-(4\gamma (\cos\theta))/P$ where $\gamma$ is the surface tension of liquid mercury, $\theta$ is the contact angle between mercury and the sample surface and P is the applied pressure.

Equipment used for pore volume measurements:
 1. Quantachrome Instruments PoreMaster 60.
 2. Analytical Balance capable of weighing to 0.0001 g.
 3. Desiccator.

Reagents used for measurements:
 1. High purity nitrogen.
 2. Triply distilled mercury.
 3. High pressure fluid (Dila AX, available from Shell Chemical Co.).
 4. Liquid nitrogen (for Hg vapor cold trap).
 5. Isopropanol or methanol for cleaning sample cells.
 6. Liquid detergent for cell cleaning.

Procedure:

The samples remain in sealed packages or as received in the dessicator until analysis. The vacuum pump is switched on, the mercury vapor cold trap is filled with liquid nitrogen, the compressed gas supply is regulated at 55 psi., and the instrument is turned on and allowed a warm up time of at least 30 minutes. The empty penetrometer cell is assembled as described in the instrument manual and its weight is recorded. The cell is installed in the low pressure station and "evacuation and fill only" is selected from the analysis menu, and the following settings are employed:

Fine Evacuation time: 1 min.
Fine Evacuation rate: 10
Coarse Evacuation time: 5 min.

The cell (filled with mercury) is then removed and weighed. The cell is then emptied into the mercury reservoir, and two tablets from each sample are placed in the cell and the cell is reassembled. The weight of the cell and sample are then recorded. The cell is then installed in the low-pressure station, the low-pressure option is selected from the menu, and the following parameters are set:

Mode: Low pressure
Fine evacuation rate: 10
Fine evacuation until: 200 μHg
Coarse evacuation time: 10 min.
Fill pressure: Contact+0.1
Maximum pressure: 50
Direction: Intrusion And Extrusion
Repeat: 0
Mercury contact angle; 140
Mercury surface tension: 480

Data acquisition is then begun. The pressure vs. cumulative volume-intruded plot is displayed on the screen. After low-pressure analysis is complete, the cell is removed from the low-pressure station and reweighed. The space above the mercury is filled with hydraulic oil, and the cell is assembled and installed in the high-pressure cavity. The following settings are used:

Mode: Fixed rate
Motor speed: 5
Start pressure: 20
End pressure: 60,000
Direction: Intrusion and extrusion
Repeat: 0
Oil fill length: 5
Mercury contact angle: 140
Mercury surface tension: 480

Data acquisition is then begun and graphic plot pressure vs. intruded volume is displayed on the screen. After the high pressure run is complete, the low- and high-pressure data files of the same sample are merged.

In one embodiment of the invention, only the core comprises one or more active ingredients. In another embodiment of this invention, only the inlaid portion comprises one or more active ingredients. In yet another embodiment of this invention, only the insert comprises one or more active ingredients. In yet another embodiment of this invention, both the core and inlaid portion comprise one or more active ingredients. In yet another embodiment of this invention, one or more of the core, the inlaid portion, or the insert comprises one or more of the active ingredients.

One of the advantages of this invention is that the inlaid portion may have a complex geometry or pattern. For example, inserts or inlaid portions previously disclosed in the prior art typically have been limited to simple shapes, e.g. shapes having circular cross-sections. Using prior art techniques, it would be extremely difficult to press fit a complex logo, for example an intagliation that causes or requires discontinuities in the surface of the substrate, core, or first portion into which it must fit. However, because the insert or inlaid portion of the present invention is obtained using a flowable material, it may be used to fill any depression in any shape or continuous pattern, or even a discontinuous pattern if multiple nozzles are employed.

Figure 3A:
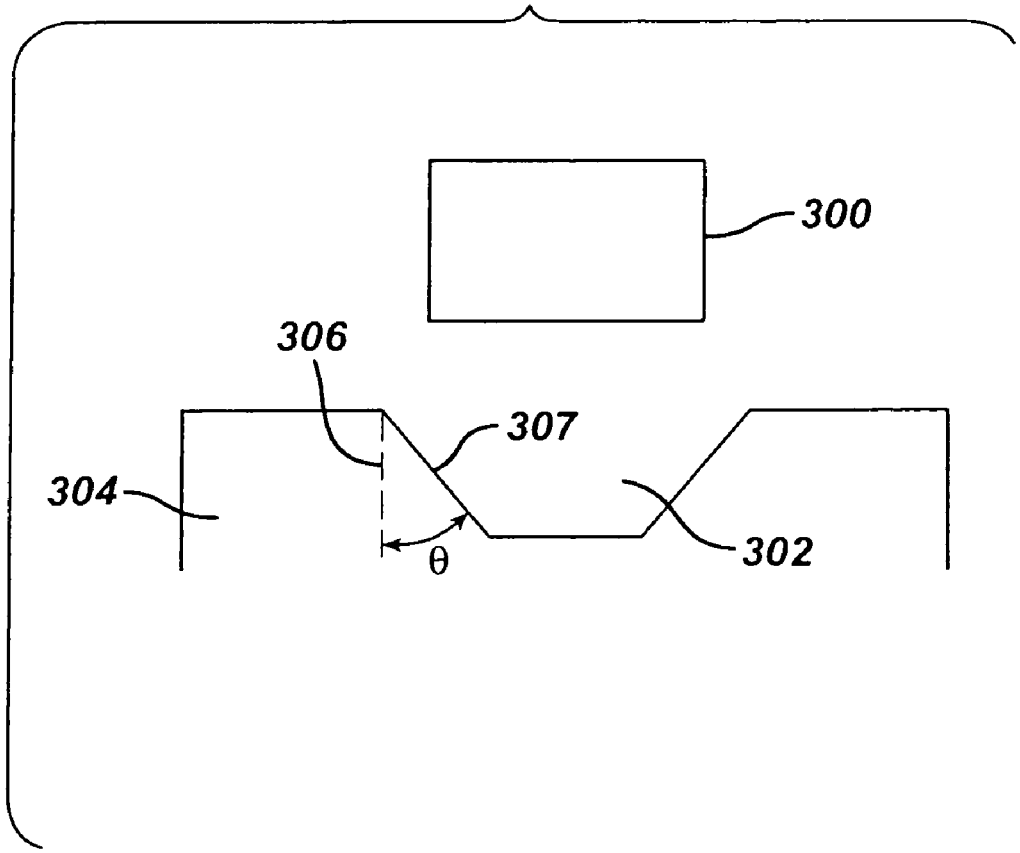
FIG. 3A depict the draft angle of a prior art composition.

A particular advantage of the present invention is that the inserts or inlaid portions may be larger in cross-section (in at least one portion) than the cavity which contains the insert or inlaid portion. For example, in one embodiment in which a second molded portion is inlaid into one or more cavities in the exterior surface of a first portion of the dosage form, the area of at least one cross-section of the second molded inlaid portion is greater than the cross-sectional area of the cavity at the surface of the first portion. In contrast, in the prior art an insert must be no larger in cross-section than the opening of the cavity which contains the insert. This may also be expressed in terms of the "draft angle" of the insert or inlaid portion. As used herein, the term "draft angle" refers to the angle defined by the side wall of the cavity and a line perpendicular to the face of the first portion, as described for example in Rosato et al., *Injection Molding Handbook*, pp. 601-04, (2d ed. 1995), the disclosure of which is incorporated herein by reference. This is illustrated in FIGS. 3A and 3B herein. In FIG. 3A, a prior art insert 300 is shown being inserted into a cavity 302 of core 304. The draft angle θ is defined by the perpendicular 306 and the sidewall 307. In the prior art, θ must have a zero or positive value. However, in this present invention θ may have a value less than zero.

In contrast, in FIG. 3B an insert or inlaid portion 500 as in this invention is shown being inserted into a cavity 502 of core 504. The draft angle θ defined by the perpendicular ray 506 emerging from the point of intersection of cavity 502 and core 504 and the side face 508 of insert 500 is less than 0°, as shown. This is because the first end 509 of insert 500 is wider than cavity 502. However, insert 500 may fill cavity 502 due to its being composed of a flowable material. Thus, insert 500 may be "keyed" or interlocked into cavity 502.

This invention will be further illustrated by the following examples, which are not meant to limit the invention in any way.

Example 1

Dosage forms of the invention are made in a continuous process using an apparatus comprising a compression module and two thermal cycle molding modules linked in series via first and second transfer devices as described at pages 14-16 of copending U.S. application Ser. No. 09/966,939, the disclosure of which is incorporated herein by reference. The dosage forms comprise a compressed core on which resides a shell comprising a first shell portion and a second shell portion that form an inlaid pattern.

The core is made from a mixture of the following ingredients: acetaminophen USP (590 mg/tablet), synthetic wax X-2068 T20 (53 mg/tablet), sodium starch glycolate (EX-PLOTAB) (13.9 mg/tablet), silicon dioxide (0.6 mg/tablet), and magnesium stearate NF (2.4 mg/tablet). These ingredients are made into a dry blend, which is compressed into cores on a compression module as described in copending U.S. application Ser. No. 09/966,509 at pages 16-27 (incorporated herein by reference) using 7/16 inch extra deep concave tablet tooling. The compression module is a double row, rotary apparatus, comprising a fill zone, insertion zone, compression zone, ejection zone, and purge zone as shown in FIG. 6 of U.S. application Ser. No. 09/966,509. The dies of the compression module are filled using vacuum assistance, with mesh screen filters located in die wall ports of each die. The resulting cores have an average weight of 660 mg, thickness of 0.306 inches, and hardness of 3.2 kp.

The cores are conveyed to a first thermal cycle molding module as described in copending U.S. application Ser. No. 09/966,497 at pages 27-51 via a first transfer device as described in copending U.S. application Ser. No. 09/966,414 at pages 51-57, the disclosure of which is incorporated herein by reference. Both the first and second transfer devices have the structure shown as 300 in FIG. 3 of copending U.S. application Ser. No. 09/966,414, and transfer the cores form the compression module to the first thermal cycle molding module and from the first thermal cycle molding module to the second thermal cycle molding module, respectively. They comprise a plurality of transfer units 304 attached in cantilever fashion to a belt 312 as shown in FIGS. 68 and 69 of copending U.S. application Ser. No. 09/966,414. The first transfer device rotates and operates in sync with the compression module and the first thermal cycle molding module to which it is coupled. The second transfer device rotates and operates in sync with the first thermal cycle molding module and the second thermal cycle molding module to which it is coupled. Transfer units 304 comprise retainers 330 for holding the cores as they travel around the transfer devices.

The tablets are coated with a first shell portion comprising red gelatin in the first thermal cycle molding module. It is of the type shown in FIG. 28A of copending U.S. application Ser. No. 09/966,939. The mold units 204 of the thermal cycle molding module comprise upper mold assemblies 214, rotatable center mold assemblies 212 and lower mold assemblies 210 as shown in FIG. 28C. Cores are transferred to the mold assemblies, which then close over the cores such that an inlaid pattern over the core is masked by the interior surface of the mold assemblies, leaving exposed a mirror image inlaid pattern on the surface of the cores. First shell flowable material, as described below, which is heated to a flowable state in a reservoir 206, is injected into the mold cavities created by the closed mold assemblies. Due to the masking, it is applied only to the exposed portions of the core. The temperature of the first shell flowable material is then decreased, hardening it. The mold assemblies open and eject the partially coated cores to the second transfer device, which transfers them to the second thermal cycle molding module.

The first shell portion comprises red gelatin coating, and is made of the following ingredients: purified water, Opatint Red DD-1761, Opatint Yellow DD-2125, and 275 Bloom Pork Skin Gelatin and 250 Bloom Bone Gelatin (150 g) added together as a mix of dry gelatin granules. A gelatin slurry is formed from these ingredients and heated to 55° C. to melt and dissolve the gelatin. The gelatin solution is held at 55° C. for approximately 3 hours (holding times at this temperature can generally range between about 2 and about 16 hours). The solution is then mixed until uniform (about 5 to 15 minutes). The gelatin solution is maintained at 55° C. with continuous mixing during its use in the first thermal cycling molding module.

The second thermal cycle molding module is also of the type shown in FIG. 26A of copending U.S. application Ser. No. 09/966,497. It applies the second shell portion (made from purified water (450 g), Opatint Yellow DD-2125 (6.2 g), 275 Bloom Pork Skin Gelatin (150 g) and 250 Bloom Bone Gelatin (150 g) in the same manner as the first shell portion) to the cores. The upper and center mold assemblies of the second thermal cycle molding module mate such that the previously exposed portion of the core, now coated with the first shell portion, are masked. This exposes the previously masked portions of the core, which remain uncoated. Second flowable material, which is heated to a flowable state in reservoir 206, is then injected into the mated upper and center mold assemblies. The temperature of the second flowable material is then decreased, hardening the second flowable material to form an inlaid pattern. The mold assemblies open and eject the finished dosage forms.

Although this invention has been illustrated by reference to specific embodiments, it will be apparent to those skilled in the art that various changes and modifications may be made which clearly fall within the scope of this invention.

The invention claimed is:

1. A dosage form comprising at least one active ingredient, a first portion which comprises an exterior surface and one or more cavities defining at least one interior surface having indentations, and a second molded portion which is inlaid into the cavities of the first portion and has an exterior surface, wherein the first and second portions are in contact at an interface, the second portion comprises a solidified thermoplastic material, and the second portion resides substantially conformally upon the indentations.

2. The dosage form of claim 1, wherein the second molded portion is substantially free of pores having a diameter of 0.5 to 5.0 microns.

3. The dosage form of claim 1, wherein the first and second portions are in intimate contact at the interface.

4. The dosage form of claim 1, wherein the first portion is a compressed tablet.

5. The dosage form of claim 1, wherein the first portion is a molded tablet.

6. The dosage form of claim 1 wherein the first portion comprises an intagliation and the second portion resides in the intagliation.

7. The dosage form of claim 1 wherein the exterior surface of the second portion is flush with the exterior surface of the first portion.

8. The dosage form of claim 1 wherein the exterior surface of the second portion is raised with respect to the exterior surface of the first portion.

9. The dosage form of claim 1 wherein the first portion consists essentially of a single homogeneous layer.

10. The dosage form of claim 1, in which the second molded portion comprises at least one active ingredient.

11. The dosage form of claim 1, in which the first portion has a first color and the inlaid second portion has a second color.

12. The dosage form of claim 1, in which the first portion comprises a first active ingredient and the inlaid second portion comprises a second active ingredient which may be the same or different than the first active ingredient.

13. The dosage form of claim 1, in which the first and second portions together provide a prearranged pattern.

14. The dosage form of claim 1, in which the first portion comprises a microelectronic device.

15. The dosage form of claim 1, in which the interior surface of one or more cavities in the first portion has a draft angle having a value less than zero.

16. The dosage form of claim 1, in which the interface is substantially coextensive with the interior surface.

17. The dosage form of claim 1, in which the first portion is discontinuous and the second portion is continuous.

18. A dosage form comprising at least one active ingredient, a core having an outer surface and a shell residing on at least a portion of the core outer surface, wherein the shell comprises a first shell portion having one or more cavities with interior surfaces and a second molded shell portion which is inlaid into the one or more cavities in the first shell portion, and the first and second shell portions are in contact at an interface and in which the interior surface of one or more cavities in the first portion has a draft angle having a value less than zero.

19. The dosage form of claim 18, in which the shell has an outer surface and the second molded shell portion extends from the outer surface of the core to the outer surface of the shell.

20. The dosage form of claim 18, in which the first and second shell portions are discontinuous.

21. The dosage form of claim 18, in which the first shell portion has a first color and the second shell portion has a second color.

22. The dosage form of claim 18, in which the core comprises a compressed powder.

23. The dosage form of claim 18, in which the core comprises an insert.

24. The dosage form of claim 23, in which the insert comprises an active ingredient.

25. The dosage form of claim 24, in which one or more of the core, the inlaid portion or the insert comprise an active ingredient.

26. The dosage form of claim 18, in which the core comprises a microelectronic device.

27. The dosage form of claim 23, in which the insert comprises a microelectronic device.

28. The dosage form of claim 18, in which either the first shell portion, second shell portion, or both have a textured outer surface.

29. The dosage form of claim 18, in which the outer surface of the shell contains a prearranged pattern.

30. The dosage form of claim 18, in which the shell comprises one or more openings therein.

31. The dosage form of claim 18, in which the outer surface of the shell is substantially smooth.

32. The dosage form of claim 18, in which the shell contains indentations, letters, symbols or a pattern.

33. The dosage form of claim 18, in which the first shell portion contains indentations, letters, symbols or a pattern.

34. The dosage form of claim 18, in which the second shell portion contains indentations, letters, symbols or a pattern.

35. The dosage form of claim 18, in which the first shell portion, second shell portion or both contain raised protrusions in the form of letters, symbols or a pattern.

36. The dosage form of claim 18, in which the inlaid portion is substantially free of pores having a diameter of 0.5-5.0 microns.

37. A dosage form comprising at least one active ingredient, a core, and a shell having a first molded shell portion which is discontinuous, and a second molded shell portion which is continuous, such that the discontinuities of the first shell portion are due to the presence of the second molded shell portion, and the first and second shell portions are compositionally different, in which the first molded shell portion and second molded shell portions are substantially free of pores having a diameter of 0.5-5.0 microns.

38. The dosage form of claim 37, wherein the first and second shell portions comprise a solidified thermoplastic material.

39. The dosage form claim 37, wherein the exterior surfaces of the first and second shell portions are coplanar.

40. The dosage form of claim 18, wherein the cavities define a plurality of side walls for receiving the inlaid portion, and the side walls have a draft angle less than zero.

41. The dosage form of claim 18, wherein the area of at least one cross-section of the second molded inlaid portion is greater than the cross-sectional area of the cavity at the surface of the first portion.

\* \* \* \* \*